United States Patent [19]

Rossmoore

[11] Patent Number: 4,608,183

[45] Date of Patent: Aug. 26, 1986

[54] SYNERGISTIC ANTIMICROBIAL OR BIOCIDAL MIXTURES INCLUDING ISOTHIAZOLONES

[75] Inventor: Harold W. Rossmoore, Oak Park, Mich.

[73] Assignee: Board of Governors of Wayne State University, Detroit, Mich.

[21] Appl. No.: 691,431

[22] Filed: Jan. 14, 1985

[51] Int. Cl.$^4$ .......................................... C10M 159/18
[52] U.S. Cl. .................................. 252/36; 252/49.5; 252/49.7; 72/42
[58] Field of Search ...................... 252/36, 49.5, 49.7; 72/42

[56] References Cited

U.S. PATENT DOCUMENTS

| | | |
|---|---|---|
| 4,129,509 | 12/1978 | Shringarpurey et al. ............ 252/49.5 |
| 4,180,473 | 12/1979 | Maurer et al. ...................... 252/49.5 |
| 4,265,899 | 5/1981 | Lewis et al. ......................... 424/270 |
| 4,279,762 | 7/1981 | Lewis et al. ........................ 252/47.5 |

Primary Examiner—Jacqueline V. Howard
Attorney, Agent, or Firm—Ian C. McLeod

[57] ABSTRACT

Antimicrobial mixtures of isothiazolones and a metal complex with a polyfunctional ligand which are synergistic are described. The mixtures particularly include mixtures of a monocopper disodium citrate as the ligand and a 5-x-2-lower alkyl 4-isothiazolin-3-one wherein x is a halo or hydrogen group as the isothiazolone. The compositions are particularly useful for metal cutting fluids wherein long duration antimicrobial activity is desired.

23 Claims, No Drawings

SYNERGISTIC ANTIMICROBIAL OR BIOCIDAL MIXTURES INCLUDING ISOTHIAZOLONES

BACKGROUND OF THE INVENTION (1) Field of the Invention

The present invention relates to synergistic antimicrobial or biocidal compositions including a metal complex of a polyfunctional organic ligand and an isothiazolone. In particular the present invention relates to the use of monocopper (II) disodium citrate as the ligand and a 5-x-2-lower alkyl 4-isothiazolin-3-one wherein x is halo or hydrogen group as the isothiazolone including particularly mixtures of these isothiazolones.

(2) Prior Art

The prior art has described metal complexes of organic ligands as antimicrobial or biocidal compounds. These include U.S. Pat. Nos. 4,055,655 to Maurer et al 4,129,589 to Shringarpurey et al and 4,180,473 to Maurer et al. The process for their manufacture is described in U.S. Pat. No. 4,278,610 to Maurer et al. The problem is that these compounds are relatively poor antimicrobials and even large amounts provided protection for only a limited period of time.

The isothiazolones are described in U.S. Pat. Nos. 3,523,121 to Lewis et al; 3,761,488 to Lewis et al; 3,957,808 to Miller et al; 4,105,431 to Lewis et al; 4,243,403 to Lewis et al; 4,252,694 to Lewis et al; 4,265,899 to Lewis et al; 4,279,762 to Lewis et al. These are very superior antimicrobial agents; however, relatively large amounts are required.

Disodium monocopper (II) citrate (MCC) is particularly described as an antimicrobial compound by U.S. Pat. No. 4,055,655. Metalworking fluid (MWF) stabilizing activity is described in U.S. Pat. No. 4,129,509 (1978)). The former patent states that the compound is effective against microorganisms growing in alkaline environments (pH 8-12) due to the stability of the metal complex form only at high pH, with dissociation into toxic copper ions occurring upon encountering the lower pH (7.0) within microbial cells.

Studies on MCC have shown that it can temporarily inhibit the growth of *Pseudomonas aeruginosa* in laboratory media and transiently reduce the cell count in MWF contaminated with Pseudomonas spp. The use of MCC as a MWF additive is becoming more widespread and an improvement in its effectiveness was needed.

Although bacteria are highly important in the biodeterioration of MWF, fungi and yeast can play a major role as well, especially in the synthetic fluids (Bennett, E. O., "The Deterioration of Metal Working Fluids," Prog. Indust. Microbiol., 13, p 121 (1974)), (Rossmoore, H.W. and Holtzman, G.H., "Growth of Fungi in Cutting Fluids," Dev. Indust. Microbiol., 15, pp 273-280 (1974)). Fusarium and Cephalosporium are prominent fungal contaminants, and among the yeasts, Candida and Trichosporon spp. are often isolated. Fungi and yeast are known to be sensitive to the toxic effects of Cu ion (Hugo, W. B. and Russell, A. D., "Types of Antimicrobial Agents," in: Principles and Practices of Disinfection, Preservation and Sterilization, Russell, A.D., W. B. Hugo, and G. A. J. Ayliffe (Eds.), Blackwell Scientific Publications, Boston, p. 69 (1982)) and consequently the effect of MCC at high pH on a representative yeast, *Candida tropicalis*, was studied.

As a result of the machining operation itself, MWF can become contaminated with selectively large concentrations of soluble iron. The high stability constant of ferric citrate can allow exchange reactions between the ferric and copper ions in binding to the citrate ligand (Ashcroft, S. J. and Mortimer, C. T., Thermochemistry of Transition Metal Complexes, Academic Press, New York (1970)). Such reactions may destroy the antimicrobial activity of MCC in alkaline environments.

Kathon TM 886 is a commercial antimicrobial solution which is a mixture of 5-chloro-2-methyl-4-isothiazolin-3-one (8.6% by wt.) and 2-methyl-4-isothiazolin-3-one (2.6% by wt.). The mixture is very effective against bacteria, fungi and algae. The required dosages are sometimes ineffective in achieving the best results due to interfering nucleophiles in the metalworking fluids. The molecular species considered as nucleophiles in these systems are amines and sulfides, the former contributed by many metalworking fluid formulae and the latter from microbial activity. Thus, efficacy is a function of the metalworking fluid composition as well as the level of microbial contamination, nucleophiles from both competing for the isothiazolones.

OBJECTS

It is therefore an object of the present invention to provide antimicrobial or biocidal compositions which are mixtures of the isothiazolones and the heavy metal complexes of the ligands which are synergistic, using less than the minimum effective dosage of the isothiazolone alone or permitting activity of the most active antimicrobial agent. It is also an object of the present invention to provide a method for the use of such synergistic compositions. These and other objects will become increasingly apparent by reference to the following description.

GENERAL DESCRIPTION

The present invention relates to a concentrated composition which comprises in admixture: a metal complex of a polyfunctional organic ligand (A); and an isothiazolone or isothiazolones (B), wherein the isothiazolone(s) (B) is present in an amount with the metal complex (A) which is less than is required for biocidal activity alone in a fluid which supports microbial growth and wherein the microbial growth in the fluid is suppressed. Preferably the microbial growth is suppressed for at least 72 hours.

Also the present invention relates to a biocidal metal working composition which comprises in admixture: a metal working fluid in admixture with a biocidal amount of a metal complex of a polyfunctional ligand (A) and an isothiazolone or isothiazolones (B), wherein the isothiazolone(s) (B) is present in an amount with the metal complex (A) which is less than is required for biocidal activity alone in the fluid and wherein microbial growth is suppressed.

Further the present invention relates to a method for producing a fluid having biocidal activity wherein the fluid supports microbial growth which comprises: providing a biocidal amount of a metal complex of a polyfunctional organic ligand (A) and an isothiazolone or isothiazolones (B) in the fluid, wherein the isothiazolone(s) (B) is present in an amount which is less than is required for biocidal activity alone in the fluid.

In particular the present invention relates to a preferred concentrated composition which comprises in admixture: a metal complex consisting essentially of disodium monocopper (II) citrate; and an isothiazolone mixture consisting essentially of 5-chloro-2 methyl-4-isothiazolin-3-one and 2-methyl-4-isothiazolin-3-one, and wherein the isothiazolones are present in an amount with the metal complex which is less than is required for biocidal activity when the concentrated composition is introduced into a fluid which supports microbial growth. The present invention further relates to a preferred method for producing a fluid having biocidal activity which comprises: providing a biocidal amount of a metal complex consisting essentially of disodium monocopper (II) citrate and an isothiazolone mixture consisting essentially of 5-chloro-2-methyl-4-isothiazolin-3-one and 2-methyl-4-isothiazolin-3-one in the fluid. Finally the present invention relates to a biocidal metal working composition which comprises in admixture: a metal working fluid in admixture with a biocidal amount of a metal complex consisting essentially of disodium monocopper (II) citrate and an isothiazolone mixture consisting essentially of 5-chloro-4-isothiazolin-3-one and 2-methyl-4-isothiazolin-3-one, wherein the isothiazolones are present in an amount which is less than is required for biocidal activity alone in the fluid.

SPECIFIC DESCRIPTION

Disodium monocopper (II) citrate MCC is available as a concentrated commercial preparation from Coolant Controls, Inc., of Cincinnati, Ohio. Analysis via the iodide reduction method revealed a concentration of 1 mole/liter of Cu ion. The preparation was sterilized by passage through an 0.22 micron membrane filter. Biocide A was a mixture of 5-chloro-2-methyl-4-isothiazolin-3-one and 2-methyl-4-isothiazolin available as Kathon ™ from Rohm and Haas of Philadelphia, Pa.

EFFECTS OF MCC ON YEAST

A *Candida tropicalis* strain isolated from spoiled MWF and kept on Sabouraud Dextrose Agar was used. The test medium was of the following composition per liter: sucrose 0.5 percent (w/v); $NH_4Cl$ 0.2 percent; $KNO_3$ 0.1 percent; $MgSO_4.7H_2O$ 0.1 percent; yeast extract 0.1 percent; beta-glycerophosphate 0.033 mole; and pH adjusted to 8.8 using KOH. *C. tropicalis* cells were grown in this medium for 36 hours to produce the experimental inoculum. A series of test flasks, each containing 100 ml of the same medium at pH 8.8, were each inoculated with 0.2 ml of the cells. MCC was added before inoculation at the following concentrations, expressed as ppm of Cu: 0, 3.3, 6.6, 33, 66, and 330. The flasks were incubated at 30° C. in a rotary shaker at 200 rpm. Growth of the cells was assessed by a visual estimation of the turbidity of the cultures at various intervals. The measurement of the increase in turbidity of a microbial culture is both a rapid and a reliable method for evaluating the increase in biomass (Spooner, D. F. and Sykes, G., "Laboratory Assessment of Antibacterial Activity," in Methods in Microbiology, 7B, Academic Press, New York, Norris, J. R. and D. W. Ribbons (Eds.), pp 211–276 (1972).

MCC AND BIOCIDE A

A sample of contaminated soluble oil (5 percent v/v)(pH 8.5) containing approximately $10^8$ cells/ml and positive for sulfate reducing bacteria was used as the test system. The bacterial contaminants were largely Pseudomonas sp. Biocide A was added to test flasks containing 30 ml of the contaminated fluid to achieve a final concentration of 2.8 ppm (30 ppm of Kathon ™). Monocopper (II) citrate was also added at the following levels: 0 ppm, 800 ppm, and 2000 ppm (01, 200 and 800 ppm as Cu). The effects on bacterial cell growth were determined by performing standard plate counts at regular intervals using 1 percent peptone (pH 7.0) as a diluent.

RESULTS AND DISCUSSION

The activity of MCC against *Pseudomonas aeruginosa* is summarized in Table 1. The compound is indeed effective at alkaline pH but this effectiveness is of a temporary nature.

TABLE 1

The Activity of Monocopper (II) Citrate Against *Pseudomonas aeruginosa* in Various Systems (as Cu)

| A. Alkaline Soy Casein Digest Medium | | |
|---|---|---|
| Time (h) | Control | 650 ppm |
| 0 | − | − |
| 5 | − | − |
| 17 | + | − |
| 22 | + | − |
| 48–72 | + | + |

| B. Alkaline Synthetic Medium | | | |
|---|---|---|---|
| Time (h) | Control | 6.5 ppm | 33 ppm |
| 0 | − | − | − |
| 10 | + | − | − |
| 27 | + | − | − |
| 30 | + | + | − |
| 48 | + | + | + |

| C. Contaminated 5% Soluble Oil Emulsion | | | | |
|---|---|---|---|---|
| | Bacterial Colony-Forming Units/ml | | | |
| Time (h) | Control | 13 ppm | 65 ppm | 325 ppm |
| 0 | $2.7 \times 10^7$ | $2.7 \times 10^7$ | $2.7 \times 10^7$ | $2.7 \times 10^7$ |
| 16 | $5.4 \times 10^7$ | $3.9 \times 10^7$ | $5 \times 10^6$ | $5.2 \times 10^5$ |
| 18 | $14.0 \times 10^7$ | $1.9 \times 10^8$ | $9 \times 10^6$ | $1.1 \times 10^6$ |
| 30 | $12.0 \times 10^7$ | $9.0 \times 10^7$ | $9.7 \times 10^7$ | $1.0 \times 10^7$ |
| 48 | $1.7 \times 10^7$ | $1.2 \times 10^7$ | $6.0 \times 10^7$ | $1 \times 10^8$ |

+ = growth
− = no growth

The effect of MCC on *C. tropicalis* at alkaline pH is seen in Table 2. Significant inhibition occurs only with the highest concentration employed (330 ppm), but even this is overcome after 50 hours of incubation.

TABLE 2

Effect of Monocopper (II) Citrate on *Candida Tropicalis* (Inorganic Salts Medium, pH 8.8)

| Time | Control | 3.3 ppm (as Cu) | 6.6 ppm | 33 ppm | 66 ppm | 330 ppm |
|---|---|---|---|---|---|---|
| 0 h | −− | −− | −− | −− | −− | −− |
| 26 h | + | + | + | + | + | −− |
| 37 h | ++ | ++ | ++ | ++ | + | −− |
| 50 h | ++ | ++ | ++ | ++ | ++ | + |
| 74 h | ++ | ++ | ++ | ++ | ++ | ++ |

−− = no growth
+ = light growth
++ = heavy growth

Table 3 shows the effects of soluble iron on the activity of MCC in alkaline solution. The flask containing the highest iron concentrations behaves identically to the control, indicating that ferric ions can successfully compete with the citrate ligand and abolish the growth-suppressing effect of MCC. Only diminishing the amount of added $FeCl_3$ will restore the full activity of this level of MCC. The presence of the ferric ion had no appreciable effect on the pH of the medium.

TABLE 3

Effect of FeCl₃ On Monocopper (II) Citrate Activity

| Time | Control | 33 ppm MCC (as Cu) | With 0.18 mM FeCl₃ | With 0.44 mM FeCl₃ | With 1.3 mM FeCl₃ |
|---|---|---|---|---|---|
| 0 h | − | − | − | − | − |
| 18 h | + | − | − | − | + |
| 36 h | + | − | − | + | + |
| 56 h | + | − | + | + | + |
| 64 h | + | + | + | + | + |

MCC = monocopper (II) citrate
− = no growth
+ = heavy growth

These results may have a deep impact on the effectiveness of MCC in controlling bacteria in MWF. Since dissolved iron is always expected in ferrous operations, MCC could easily be rendered ineffective in those systems.

The results of MCC in combination with Biocide A are shown in Table 4. The enhancement of activity against the viable cell count in this fluid is marked. The level of Biocide A was deliberately chosen below the normal recommended level of 11.2 ppm to insure that any synergism, if expressed, could be clearly seen. Monocopper (II) citrate at comparable levels in another MWF system did not produce a comparable reduction in numbers (Table 1).

TABLE 4

Monocopper (II) Citrate and Biocide A in 5% Soluble Oil Metalworking Fluid. Reduction of Cell Count (Cells/ML) As a Function of Time.

| Time | Control | 2.8 ppm A | 2.8 ppm A + 800 ppm MCC* | 2.8 ppm A + 2000 ppm MCC** |
|---|---|---|---|---|
| 0 h | $2.2 \times 10^8$ | $2.2 \times 10^8$ | $2.2 \times 10^8$ | $2.2 \times 10^8$ |
| 6 h | N/A | $1.3 \times 10^8$ | $4.4 \times 10^7$ | $2.5 \times 10^7$ |
| 12 h | N/A | $1.2 \times 10^8$ | $6.8 \times 10^5$ | $5.3 \times 10^5$ |
| 20 h | N/A | $2.8 \times 10^8$ | $7.8 \times 10^3$ | $5.2 \times 10^3$ |
| 33 h | $9.4 \times 10^8$ | $4.2 \times 10^8$ | $<10^2$ | $<10^2$ |
| 50 h | $7.1 \times 10^8$ | $7.5 \times 10^8$ | $<10^2$ | $<10^2$ |

MCC = monocopper (II) citrate
N/A = counts not available
*200 ppm as copper
**500 ppm as copper Although the first patent describing MCC (U.S. Pat. No. 4,055,655) was based on its antimicrobial activity, it should be stressed that subsequent commercialization has been directed toward its use as a MWF stabilizer, especially for soluble oils (U.S. Pat. No. 4,129,509). The reason for this is clear from Tables 1 to 3.

As can be seen from Table 4 the results with mixtures of MCC with the Biocide A show synergism. Equivalent results can be achieved with other isothiazolones and metal complexes of polyfunctional organic ligands, particularly heavy metal citrates such as MCC.

The preferred range of metal ion in the complex is between 1.5 ppm and 100 ppm, but can be as high as 500 ppm. More than 1.5 ppm metal in the complex is preferred. The preferred range of the isothiazolone is between about 2.8 and 21 ppm. The preferred weight ratio of 5-chloro-2-methyl-4-isothiazolin-3-one to 2-methyl-4-istohiazolin-3-one is between about 3 to 1 and 10 to 1 and most preferred is 3 to 1 and 4 to 1.

It is intended that the foregoing description be only illustrative of the present invention and that the present invention be limited only by the hereinafter appended claims.

I claim:

1. A concentrated composition which comprises in admixture:
   (a) a heavy metal complex of a polyfunctional organic ligand(A); and
   (b) an isothiazolone or isothiazolones (B), wherein the isothiazolone(s) (B) is present in an amount with the metal complex (A) which is less than is required for biocidal activity alone in a fluid which supports microbial growth, wherein the metal complex provides a metal ion in the fluid which is toxic to microbial growth with the isothiazolone(s) and wherein between 1.5 and 500 ppm of metal ion is provided in the fluid from the metal complex and wherein the microbial growth in the fluid is suppressed for over 50 hours in the presence of ferric ion.

2. The biocidal composition of claim 1 wherein in the fluid the concentration of (A) is between from about 1.5 ppm to about 100 ppm of metal ion derived from the metal complex and the concentration of (B) is between from about 2.8 ppm to about 21 ppm.

3. The biocidal composition of claim 1 wherein the isothiazolone is a 5-x-2-lower alkyl-4-substituted 4-isothiazolin-3-one wherein x is halo or hydrogen and the organic polyfunctional ligand is a citrate.

4. A biocidal metal working composition which comprises in admixture:
   (a) a metal working fluid in admixture with a biocidal amount of
   (b) a heavy metal complex of a polyfunctional ligand (A) and an isothiazolone or isothiazolones (B), wherein the isothiazolones(s) (B) is present in an amount with the metal complex (A) which is less than is required for biocidal activity alone in the fluid, wherein the metal complex provides a metal ion in the fluid which is toxic to microbial growth with the isothiazolone(s), wherein between 1.5 and 500 ppm of metal ion is provided in the fluid from the metal complex and wherein microbial growth is suppressed for over 50 hours in the presence of ferric ion.

5. The biocidal composition of claim 4 wherein the concentration of (A) is between from about 1.5 ppm to about 100 ppm of metal ion derived from the metal complex and the concentration of (B) is between from about 2.8 ppm to about 21 ppm.

6. The biocidal composition of claim 4 wherein the composition contains more than 1.5 ppm of the metal from (A).

7. The biocidal composition of claim 4 wherein the isothiazolone is a 5-x-2-lower alkyl-4-isothiazoline-3-one wherein x is halo or hydrogen and wherein the organic polyfunctional ligand is a citrate.

8. A method for producing a fluid having biocidal activity wherein the fluid supports microbial growth which comprises:
   providing a biocidal amount of a heavy metal complex of a polyfunctional organic ligand (A) and an isothiazolone or isothiazolines (B) in the fluid, wherein the isothiazolone(s) (B) is present in an amount which is less than is required for biocidal activity alone in the fluid wherein the metal complex provides a metal ion in the fluid which is toxic to microbial growth with the isothiazolone(s), wherein between 1.5 and 500 ppm of metal ion is provided in the fluid from the metal complex and wherein microbial growth is suppressed for over 50 hours in the presence of ferric ion.

9. The biocidal composition of claim 8 wherein the concentration of (A) is between from about 1.5 ppm to about 100 ppm of metal ion derived from the metal complex and the concentration of (B) is between from about 3.5 ppm to about 20 ppm.

10. The method of claim 8 wherein the composition contains more than 1.5 ppm of metal from (A).

11. The method of claim 8 wherein the isothiazolone is a 5-x-4-isothiazolin-3-one wherein x is halo or hydrogen and wherein the organic polyfunctional ligand is a citrate.

12. A concentrated composition which comprises in admixture:
   (a) a metal complex consisting essentially of disodium monocopper (II) citrate; and
   (b) an isothiazolone mixture consisting essentially of 5-chloro-2-methyl-4-isothiazolin-3-one and 2-methyl-4-isothiazolin-3-one; and wherein the isothiazolones are present in amount with the metal complex which is less than is required for biocidal activity when the concentrated composition is introduced into a fluid which supports microbial growth, wherein between 1.5 and 500 ppm of copper ion is provided in the fluid from the metal complex and wherein microbial growth is suppressed for over 50 hours in the presence of ferric ion.

13. The composition of claim 12 wherein the 5-chloro-2-methyl-4-isothiazolin-3-one and 2-methyl-4-isothiazolin-3-one are in a weight ratio of from about 3 to 1 to about 4 to 1.

14. The composition of claim 12 wherein the composition can be mixed with the fluid to produce an amount of the isothiazolone which is between from about 3.5 to 21 ppm and the metal from the metal complex is from about 1.5 to about 21 ppm.

15. The composition of claim 14 wherein the isothiazolones are present in an amount between about 2.8 and 21 ppm and the metal complex is present in an amount between 250 and 2000 ppm.

16. A method for producing a fluid having biocidal activity which comprises:
   providing a biocidal amount of a metal complex consisting essentially of disodium monocopper (II) citrate and an isothiazolone mixture consisting essentially of 5-chloro-2-methyl-4-isothiazolin-3-one and 2-methyl-4-isothiazolin-3-one in the fluid, wherein between 1.5 and 500 ppm of copper ion is provided in the fluid from the metal complex and wherein microbial growth is suppressed for over 50 hours in the presence of ferric ion.

17. The method of claim 16 wherein the 5-chloro-2-methyl-4-isothiazolin-3-one and 2-methyl-4-isothiazolin-3-one are in a weight ratio of about 3 to 1 and 10 to 1.

18. The method of claim 16 wherein an amount of the isothiazolones which is between about 2.8 and 21 ppm and an amount of the metal from the metal complex which is between about 1.5 and 21 ppm is provided in the fluid.

19. The method of claim 16 wherein the isothiazolones are present in an amount between about 2.8 and 21 ppm and the metal complex is present in an amount between 250 and 2000 ppm.

20. A biocidal metal working composition which comprises in admixture:
   (a) a metal working fluid in admixture with a biocidal amount of
   (b) a metal complex consisting essentially of disodium monocopper(II) citrate and an isothiazolone mixture consisting essentially of 5-chloro-4-isothiazolin-3-one and 2-methyl-4-isothiazolin-3-one, wherein the isothiazolones are present in an amount which is less than is required for biocidal activity alone in the fluid, wherein between 1.5 and 500 ppm of copper is provided in the fluid from the metal complex and wherein microbial growth is suppressed for over 50 hours in the presence of ferric ion.

21. The composition of claim 20 wherein the 5-chloro-2-methyl-4-isothiazolin-3-one and 2-methyl-4-isothiazolin-3-one are in a weight ratio of about 3 to 1 and 10 to 1.

22. The composition of claim 20 wherein the composition can be mixed with the fluid to produce an amount of the isothiazolones which is between about 2.8 and 21 ppm and an amount of the metal from the metal complex which is between about 1.5 and 21 ppm.

23. The composition of claim 20 wherein the isothiazolones are present in an amount of about 2.8 and 21 ppm and the metal complex is present in an amount between 250 and 2000 ppm.

* * * * *